(12) United States Patent
Wolfe

(10) Patent No.: US 8,577,623 B2
(45) Date of Patent: Nov. 5, 2013

(54) ANTI-TERRORISM WATER QUALITY MONITORING SYSTEM

(75) Inventor: Thomas D. Wolfe, Grass Valley, CA (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 13/619,775

(22) Filed: Sep. 14, 2012

(65) Prior Publication Data
US 2013/0013259 A1    Jan. 10, 2013

Related U.S. Application Data

(60) Continuation of application No. 12/710,451, filed on Feb. 23, 2010, now Pat. No. 8,504,305, which is a division of application No. 12/272,018, filed on Nov. 17, 2008, now Pat. No. 7,698,073, which is a continuation of application No. 10/392,112, filed on Mar. 19, 2003, now Pat. No. 7,454,295, which is a continuation-in-part of application No. 10/055,225, filed on Oct. 26, 2001, now Pat. No. 6,560,543, which is a continuation-in-part of application No. 09/213,781, filed on Dec. 17, 1998, now Pat. No. 6,332,110.

(51) Int. Cl.
*G06F 19/00* (2011.01)

(52) U.S. Cl.
USPC ............. 702/22; 702/30; 702/31; 210/141; 210/634; 210/638; 210/660; 700/270; 700/271

(58) Field of Classification Search
USPC ............. 702/22, 30, 31, 188; 700/270–271; 210/141, 634, 638, 660
See application file for complete search history.

(56) References Cited

U.S. PATENT DOCUMENTS

| | | | |
|---|---|---|---|
| 4,626,992 A | 12/1986 | Greaves et al. |
| 4,830,757 A | 5/1989 | Lynch et al. |
| 5,227,038 A | 7/1993 | Smalley et al. |
| 5,300,203 A | 4/1994 | Smalley |

(Continued)

FOREIGN PATENT DOCUMENTS

| | | |
|---|---|---|
| CA | 2283502 A1 | 9/1998 |
| EP | 0854839 A1 | 7/1998 |

(Continued)

OTHER PUBLICATIONS

International Search Report and Written Opinion dated Jul. 10, 2012, in Application No. PCT/IB2011/055238.

(Continued)

*Primary Examiner* — Jonathan C Teixeira Moffat
*Assistant Examiner* — Hien Vo
(74) *Attorney, Agent, or Firm* — Miles & Stockbridge P.C.

(57) ABSTRACT

An Anti-Terrorism water quality monitoring system for continuously monitoring a potable water treatment system and related potable water distribution network that provides potable water to a municipality, city, housing development or other potable water consumer. The system includes the collection of data from the water distribution system and from the water treatment facility and from advanced separation processes which are integrated into analytical instruments. The data collected are stored in a remote database on a remote server computer or bank of computers and accessible by Homeland Security or its designated agency. Preferred parameters of monitoring include the turbidity and disinfectant such as chlorine, hypochlorous acid, sodium hypochlorite, calcium hypochlorite, ozone, chlorine dioxide, chloramines, hydrogen peroxide, peracetic acid.

19 Claims, 1 Drawing Sheet

(56) References Cited

U.S. PATENT DOCUMENTS

| | | |
|---|---|---|
| 5,315,880 A | 5/1994 | Bailey |
| 5,386,373 A | 1/1995 | Keeler et al. |
| 5,451,314 A | 9/1995 | Neuenschwander |
| 5,483,164 A | 1/1996 | Moss et al. |
| 5,492,632 A | 2/1996 | Reber |
| 5,506,791 A | 4/1996 | Hungerford et al. |
| 5,544,531 A | 8/1996 | Heckman |
| 5,553,492 A | 9/1996 | Barrett et al. |
| 5,556,517 A | 9/1996 | Smalley |
| 5,591,312 A | 1/1997 | Smalley |
| 5,608,171 A | 3/1997 | Hunter et al. |
| 5,619,631 A * | 4/1997 | Schott ............................. 345/440 |
| 5,631,744 A | 5/1997 | Takeuchi et al. |
| 5,633,809 A | 5/1997 | Wissenbach et al. |
| 5,644,088 A | 7/1997 | Heckman |
| 5,691,914 A | 11/1997 | Randolph |
| 5,739,376 A | 4/1998 | Bingel |
| 5,754,451 A | 5/1998 | Williams |
| 5,757,659 A * | 5/1998 | Arai et al. ........................ 702/22 |
| 5,811,688 A | 9/1998 | Marsh et al. |
| 5,826,029 A | 10/1998 | Gore et al. |
| 5,832,410 A | 11/1998 | Lin et al. |
| 5,835,724 A | 11/1998 | Smith |
| 5,865,718 A | 2/1999 | Chan |
| 5,970,426 A | 10/1999 | Mandel et al. |
| 5,993,662 A | 11/1999 | Garr et al. |
| 5,997,750 A | 12/1999 | Rozelle et al. |
| 6,023,223 A | 2/2000 | Baxter, Jr. |
| 6,061,603 A | 5/2000 | Papadopoulos et al. |
| 6,064,148 A | 5/2000 | Tolt et al. |
| 6,097,995 A * | 8/2000 | Tipton et al. ................... 700/266 |
| 6,129,901 A | 10/2000 | Moskovits et al. |
| 6,149,775 A | 11/2000 | Tsuboi et al. |
| 6,162,926 A | 12/2000 | Murphy et al. |
| 6,183,714 B1 | 2/2001 | Smalley et al. |
| 6,208,943 B1 | 3/2001 | Randolph et al. |
| 6,265,466 B1 | 7/2001 | Glatkowski et al. |
| 6,305,944 B1 | 10/2001 | Henry et al. |
| 6,317,639 B1 | 11/2001 | Hansen |
| 6,332,110 B1 | 12/2001 | Wolfe |
| 6,346,023 B1 | 2/2002 | Tsuboi et al. |
| 6,356,205 B1 | 3/2002 | Salvo et al. |
| 6,359,444 B1 | 3/2002 | Grimes |
| 6,370,448 B1 | 4/2002 | Eryurek |
| 6,389,331 B1 | 5/2002 | Jensen et al. |
| 6,399,785 B1 | 6/2002 | Murphy et al. |
| 6,401,526 B1 | 6/2002 | Dai et al. |
| 6,448,412 B1 | 9/2002 | Murphy et al. |
| 6,493,208 B1 | 12/2002 | Piche et al. |
| 6,509,619 B1 | 1/2003 | Kendall et al. |
| 6,538,153 B1 | 3/2003 | Hirsch et al. |
| 6,560,543 B2 | 5/2003 | Wolfe et al. |
| 6,645,455 B2 | 11/2003 | Margrave et al. |
| 6,672,077 B1 | 1/2004 | Bradley et al. |
| 6,683,783 B1 | 1/2004 | Smalley et al. |
| 6,692,717 B1 | 2/2004 | Smalley et al. |
| 6,712,864 B2 | 3/2004 | Horiuchi et al. |
| 6,743,408 B2 | 6/2004 | Lieber et al. |
| 6,748,748 B2 | 6/2004 | Bradley et al. |
| 6,749,827 B2 | 6/2004 | Smalley et al. |
| 6,752,977 B2 | 6/2004 | Smalley et al. |
| 6,756,025 B2 | 6/2004 | Colbert et al. |
| 6,756,026 B2 | 6/2004 | Colbert et al. |
| 6,762,237 B2 | 7/2004 | Glatkowski et al. |
| 6,790,425 B1 | 9/2004 | Smalley et al. |
| 6,811,457 B2 | 11/2004 | Cheng et al. |
| 6,824,755 B2 | 11/2004 | Colbert et al. |
| 6,827,918 B2 | 12/2004 | Margrave et al. |
| 6,830,679 B2 | 12/2004 | Tsuihiji et al. |
| 6,836,737 B2 | 12/2004 | Petite et al. |
| 6,845,336 B2 | 1/2005 | Kodukkula et al. |
| 6,847,739 B2 | 1/2005 | Jostschulte |
| 6,852,410 B2 | 2/2005 | Veedu et al. |
| 6,858,197 B1 | 2/2005 | Delzeit |
| 6,863,942 B2 | 3/2005 | Ren et al. |
| 6,872,330 B2 | 3/2005 | Mack et al. |
| 6,875,412 B2 | 4/2005 | Margrave et al. |
| 6,890,506 B1 | 5/2005 | Harutyunyan et al. |
| 6,899,945 B2 | 5/2005 | Smalley et al. |
| 6,900,264 B2 | 5/2005 | Kumar et al. |
| 6,913,789 B2 | 7/2005 | Smalley et al. |
| 6,921,575 B2 | 7/2005 | Horiuchi et al. |
| 6,936,233 B2 | 8/2005 | Smalley et al. |
| 6,936,653 B2 | 8/2005 | McElrath et al. |
| 6,939,525 B2 | 9/2005 | Colbert et al. |
| 6,949,237 B2 | 9/2005 | Smalley et al. |
| 6,954,701 B2 | 10/2005 | Wolfe |
| 6,969,504 B2 | 11/2005 | Smalley et al. |
| 6,979,709 B2 | 12/2005 | Smalley et al. |
| 6,986,853 B2 | 1/2006 | Glatkowski et al. |
| 6,988,925 B2 | 1/2006 | Arthur et al. |
| 7,008,563 B2 | 3/2006 | Smalley et al. |
| 7,008,604 B2 | 3/2006 | Smalley et al. |
| 7,014,737 B2 | 3/2006 | Harutyunyan et al. |
| 7,029,646 B2 | 4/2006 | Margrave et al. |
| 7,036,324 B2 | 5/2006 | Bradley et al. |
| 7,041,620 B2 | 5/2006 | Smalley et al. |
| 7,048,999 B2 | 5/2006 | Smalley et al. |
| 7,049,353 B2 | 5/2006 | Conroy et al. |
| 7,052,666 B2 | 5/2006 | Colbert et al. |
| 7,052,668 B2 | 5/2006 | Smalley et al. |
| 7,060,241 B2 | 6/2006 | Glatkowski |
| 7,061,749 B2 | 6/2006 | Liu et al. |
| 7,067,098 B2 | 6/2006 | Colbert et al. |
| 7,070,651 B1 | 7/2006 | Tolt et al. |
| 7,070,754 B2 | 7/2006 | Smalley et al. |
| 7,070,810 B2 | 7/2006 | Hirsch et al. |
| 7,074,310 B2 | 7/2006 | Smalley et al. |
| 7,076,871 B2 | 7/2006 | Horiuchi et al. |
| 7,087,207 B2 | 8/2006 | Smalley et al. |
| 7,090,819 B2 | 8/2006 | Smalley et al. |
| 7,094,679 B1 | 8/2006 | Li et al. |
| 7,108,841 B2 | 9/2006 | Smalley et al. |
| 7,118,693 B2 | 10/2006 | Glatkowski et al. |
| 7,121,158 B2 | 10/2006 | Scott et al. |
| 7,176,877 B2 | 2/2007 | Tikhonski et al. |
| 7,179,561 B2 | 2/2007 | Niu et al. |
| 7,182,914 B2 | 2/2007 | Lai et al. |
| 7,189,314 B1 | 3/2007 | Pace et al. |
| 7,189,430 B2 | 3/2007 | Ajayan et al. |
| 7,195,754 B1 | 3/2007 | Glatkowski et al. |
| 7,204,970 B2 | 4/2007 | Smalley et al. |
| 7,217,650 B1 | 5/2007 | Ng et al. |
| 7,227,140 B2 | 6/2007 | Skidmore et al. |
| 7,250,148 B2 | 7/2007 | Yang et al. |
| 7,276,266 B1 | 10/2007 | Khare et al. |
| 7,282,191 B1 | 10/2007 | Choi et al. |
| 7,285,198 B2 | 10/2007 | Douglas |
| 7,303,875 B1 | 12/2007 | Bock et al. |
| 7,338,648 B2 | 3/2008 | Harutyunyan et al. |
| 7,338,915 B1 | 3/2008 | Smalley et al. |
| 7,342,479 B2 | 3/2008 | Glatkowski et al. |
| 7,342,506 B2 | 3/2008 | Paoli et al. |
| 7,345,307 B2 | 3/2008 | Pan et al. |
| 7,354,563 B2 | 4/2008 | Smalley et al. |
| 7,357,906 B2 | 4/2008 | Colbert et al. |
| 7,357,983 B2 | 4/2008 | Pfefferle et al. |
| 7,365,395 B2 | 4/2008 | Stumbo et al. |
| 7,378,040 B2 | 5/2008 | Luo et al. |
| 7,390,477 B2 | 6/2008 | Smalley et al. |
| 7,390,767 B2 | 6/2008 | Smalley et al. |
| 7,426,848 B1 | 9/2008 | Li et al. |
| 7,428,046 B2 | 9/2008 | Wang et al. |
| 7,452,735 B2 | 11/2008 | Li et al. |
| 7,454,295 B2 | 11/2008 | Wolfe |
| 7,465,494 B2 | 12/2008 | Ren et al. |
| 7,466,533 B2 | 12/2008 | Chow et al. |
| 7,468,315 B2 | 12/2008 | Buretea et al. |
| 7,470,620 B2 | 12/2008 | Dubin et al. |
| 7,473,411 B2 | 1/2009 | Ajayan et al. |
| 7,473,436 B1 | 1/2009 | Khare et al. |
| 7,479,240 B2 | 1/2009 | Jhi et al. |
| 7,514,369 B2 | 4/2009 | Li et al. |
| 7,515,333 B1 | 4/2009 | Empedocies |

(56) References Cited

U.S. PATENT DOCUMENTS

| | | |
|---|---|---|
| 7,522,040 B2 | 4/2009 | Passmore et al. |
| 7,553,371 B2 | 6/2009 | Dubrow et al. |
| 7,553,471 B2 | 6/2009 | Ohashi et al. |
| 7,557,028 B1 | 7/2009 | Scher et al. |
| 7,560,134 B2 | 7/2009 | Yaniv et al. |
| 7,560,136 B2 | 7/2009 | Ward et al. |
| 7,560,366 B1 | 7/2009 | Romano et al. |
| 7,563,722 B2 | 7/2009 | Yaniv et al. |
| 7,566,945 B2 | 7/2009 | Choi et al. |
| 7,569,503 B2 | 8/2009 | Pan et al. |
| 7,575,720 B2 | 8/2009 | Novak et al. |
| 7,575,933 B2 | 8/2009 | Gabriel et al. |
| 7,581,645 B2 | 9/2009 | Ho et al. |
| 7,595,528 B2 | 9/2009 | Duan et al. |
| 7,596,415 B2 | 9/2009 | Brabec et al. |
| 7,597,788 B2 | 10/2009 | Visel et al. |
| 7,611,740 B2 | 11/2009 | Jiang et al. |
| 7,611,906 B2 | 11/2009 | Yaniv |
| 7,623,972 B1 | 11/2009 | Li et al. |
| 7,628,974 B2 | 12/2009 | Grill et al. |
| 7,630,227 B2 | 12/2009 | Tran |
| 7,632,548 B2 | 12/2009 | Yaniv |
| 7,635,503 B2 | 12/2009 | Dominguez et al. |
| 7,641,938 B2 | 1/2010 | Liu et al. |
| 7,645,397 B2 | 1/2010 | Parce et al. |
| 7,647,813 B2 | 1/2010 | Pavlovsky |
| 7,651,769 B2 | 1/2010 | Dubrow |
| 7,651,944 B2 | 1/2010 | Duan et al. |
| 7,652,418 B2 | 1/2010 | Choi et al. |
| 7,655,497 B1 | 2/2010 | Yu et al. |
| 7,667,296 B2 | 2/2010 | Stumbo et al. |
| 7,687,981 B2 | 3/2010 | Parsapour |
| 7,691,720 B2 | 4/2010 | Furukawa et al. |
| 7,695,609 B2 | 4/2010 | Soundarrajan et al. |
| 7,696,272 B2 | 4/2010 | Li et al. |
| 7,698,073 B2 | 4/2010 | Wolfe |
| 7,701,014 B2 | 4/2010 | Mostarshed et al. |
| 7,701,428 B2 | 4/2010 | Stumbo et al. |
| 7,704,479 B2 | 4/2010 | Rinzler et al. |
| 7,704,547 B1 | 4/2010 | Delzeit et al. |
| 7,714,386 B2 | 5/2010 | Pesetski et al. |
| 7,714,398 B2 | 5/2010 | Ben-Barak et al. |
| 7,728,520 B2 | 6/2010 | Yaniv et al. |
| 7,736,209 B2 | 6/2010 | Mao et al. |
| 7,736,979 B2 | 6/2010 | Farrow et al. |
| 7,741,197 B1 | 6/2010 | Duan et al. |
| 7,745,498 B2 | 6/2010 | Pereira et al. |
| 7,749,477 B2 | 7/2010 | Jiang et al. |
| 7,750,235 B2 | 7/2010 | Scher et al. |
| 7,754,524 B2 | 7/2010 | Dubrow et al. |
| 7,755,038 B2 | 7/2010 | Niu et al. |
| 7,755,115 B2 | 7/2010 | Awano |
| 7,762,121 B2 | 7/2010 | Ng et al. |
| 7,767,067 B2 | 8/2010 | Silveri |
| 7,767,102 B2 | 8/2010 | Lemmi et al. |
| 7,767,270 B1 | 8/2010 | Khare et al. |
| 7,776,758 B2 | 8/2010 | Duan et al. |
| 7,776,760 B2 | 8/2010 | Taylor |
| 7,782,462 B2 | 8/2010 | Pavlovsky |
| 7,784,531 B1 | 8/2010 | Li et al. |
| 7,785,922 B2 | 8/2010 | Robbins |
| 7,786,024 B2 | 8/2010 | Stumbo et al. |
| 7,786,402 B2 | 8/2010 | Fink et al. |
| 7,791,258 B2 | 9/2010 | Yaniv et al. |
| 7,794,600 B1 | 9/2010 | Buretea et al. |
| 7,795,125 B2 | 9/2010 | Buretea et al. |
| 7,801,687 B1 | 9/2010 | Li et al. |
| 2001/0020195 A1 | 9/2001 | Patel et al. |
| 2001/0053992 A1 | 12/2001 | Eto et al. |
| 2002/0023479 A1 | 2/2002 | Burge et al. |
| 2002/0130069 A1 | 9/2002 | Moskoff |
| 2002/0133270 A1 | 9/2002 | Hung et al. |
| 2003/0052585 A1 | 3/2003 | Guillorn et al. |
| 2003/0089899 A1 | 5/2003 | Lieber et al. |
| 2003/0124717 A1 | 7/2003 | Awano et al. |
| 2003/0174070 A1 | 9/2003 | Garrod et al. |
| 2003/0207326 A1 | 11/2003 | Su et al. |
| 2004/0026684 A1 | 2/2004 | Empedocles |
| 2004/0066313 A1 | 4/2004 | Ong et al. |
| 2004/0132070 A1 | 7/2004 | Star et al. |
| 2004/0136866 A1 | 7/2004 | Pontis et al. |
| 2004/0245209 A1 | 12/2004 | Jung et al. |
| 2005/0046017 A1 | 3/2005 | Dangelo |
| 2005/0136483 A1 | 6/2005 | Carlson |
| 2005/0186333 A1 | 8/2005 | Douglas |
| 2005/0221473 A1 | 10/2005 | Dubin et al. |
| 2005/0224220 A1 | 10/2005 | Li et al. |
| 2005/0269285 A1 | 12/2005 | Jung et al. |
| 2006/0014155 A1 | 1/2006 | Hamers et al. |
| 2006/0112983 A1 | 6/2006 | Parce et al. |
| 2006/0124028 A1 | 6/2006 | Huang et al. |
| 2006/0240218 A1 | 10/2006 | Parce |
| 2006/0257637 A1 | 11/2006 | Pereira et al. |
| 2006/0275914 A1 | 12/2006 | Henley et al. |
| 2007/0044295 A1 | 3/2007 | Chen |
| 2007/0045128 A1 | 3/2007 | Krathefer et al. |
| 2007/0132043 A1 | 6/2007 | Bradley et al. |
| 2007/0140930 A1 | 6/2007 | Novak et al. |
| 2007/0155064 A1 | 7/2007 | Chen et al. |
| 2007/0163965 A1 | 7/2007 | Wolfe |
| 2007/0238209 A1 | 10/2007 | Yaniv et al. |
| 2007/0246364 A1 | 10/2007 | Amlani et al. |
| 2008/0035481 A1 | 2/2008 | McCormack et al. |
| 2008/0142361 A1 | 6/2008 | Han et al. |
| 2008/0150009 A1 | 6/2008 | Chen |
| 2008/0152839 A1 | 6/2008 | Han et al. |
| 2008/0221806 A1 | 9/2008 | Bryant et al. |
| 2008/0237540 A1 | 10/2008 | Dubrow |
| 2008/0246076 A1 | 10/2008 | Chen |
| 2008/0280069 A1 | 11/2008 | Parce et al. |
| 2008/0280780 A1 | 11/2008 | Hamers et al. |
| 2009/0035570 A1 | 2/2009 | Mao et al. |
| 2009/0045061 A1 | 2/2009 | Farrow et al. |
| 2009/0058431 A1 | 3/2009 | Dass et al. |
| 2009/0072192 A1 | 3/2009 | Seal et al. |
| 2009/0095704 A1 | 4/2009 | Mao et al. |
| 2009/0123343 A1 | 5/2009 | Kwiatkowski |
| 2009/0124025 A1 | 5/2009 | Hamilton et al. |
| 2009/0138240 A1 | 5/2009 | Wolfe |
| 2009/0192429 A1 | 7/2009 | Daniels et al. |
| 2009/0198117 A1 | 8/2009 | Cooper et al. |
| 2009/0230380 A1 | 9/2009 | Leon et al. |
| 2009/0242429 A1 | 10/2009 | Sitdikov et al. |
| 2009/0242854 A1 | 10/2009 | Li et al. |
| 2009/0252886 A1 | 10/2009 | Barker et al. |
| 2009/0261186 A1 | 10/2009 | Fink et al. |
| 2009/0274833 A1 | 11/2009 | Li et al. |
| 2009/0278556 A1 | 11/2009 | Man et al. |
| 2009/0286383 A1 | 11/2009 | Jiang et al. |
| 2009/0325370 A1 | 12/2009 | Yang et al. |
| 2010/0000762 A1 | 1/2010 | Yang et al. |
| 2010/0055349 A1 | 3/2010 | Gaitas et al. |
| 2010/0062178 A1 | 3/2010 | Zhang et al. |
| 2010/0068406 A1 | 3/2010 | Man |
| 2010/0072429 A1 | 3/2010 | Rajala et al. |
| 2010/0089122 A1 | 4/2010 | Abdullah et al. |
| 2010/0102245 A1 | 4/2010 | Jiang et al. |
| 2010/0104808 A1 | 4/2010 | Fan et al. |
| 2010/0116666 A1 | 5/2010 | Park et al. |
| 2010/0127167 A1 | 5/2010 | Schropp, Jr. et al. |
| 2010/0140213 A1 | 6/2010 | Mizukami et al. |
| 2010/0143234 A1 | 6/2010 | Kajiuyra et al. |
| 2010/0153021 A1 | 6/2010 | Wolfe |
| 2010/0167011 A1 | 7/2010 | Dubrow |
| 2010/0167512 A1 | 7/2010 | Pan et al. |
| 2010/0173228 A1 | 7/2010 | Wallace et al. |
| 2010/0204924 A1 | 8/2010 | Wolfe et al. |
| 2010/0332149 A1 | 12/2010 | Scholpp |
| 2011/0125412 A1 | 5/2011 | Salzer et al. |
| 2012/0125771 A1 | 5/2012 | Salzer et al. |

(56) References Cited

U.S. PATENT DOCUMENTS

FOREIGN PATENT DOCUMENTS

| | | |
|---|---|---|
| EP | 1015384 A1 | 7/2000 |
| EP | 1404908 B1 | 11/2007 |
| EP | 1864122 A2 | 12/2007 |
| EP | 1623437131 | 12/2007 |
| EP | 1954387 A2 | 8/2008 |
| EP | 1976431 A2 | 10/2008 |
| EP | 1836104 B1 | 1/2009 |
| EP | 2018549 A2 | 1/2009 |
| EP | 2047531 A2 | 4/2009 |
| EP | 2012589 B1 | 7/2009 |
| EP | 2083928 A1 | 8/2009 |
| EP | 1556878 B1 | 4/2010 |
| JP | 3958792 B2 | 8/2007 |
| JP | 3962376 B2 | 8/2007 |
| JP | 2008/260073 | 10/2008 |
| JP | 4381428 B2 | 12/2009 |
| WO | WO 97/09272 A1 | 3/1997 |
| WO | WO 00/36412 A1 | 6/2000 |
| WO | WO 01/80494 | 10/2001 |
| WO | WO 03/024798 A1 | 3/2003 |
| WO | WO 03/038685 A2 | 5/2003 |
| WO | WO 03/050036 A1 | 6/2003 |
| WO | WO 03/078317 A1 | 9/2003 |
| WO | WO 2004/024407 A1 | 3/2004 |
| WO | WO 2004/052559 A2 | 6/2004 |
| WO | WO 2004/069737 A2 | 8/2004 |
| WO | WO 2004/097853 A1 | 11/2004 |
| WO | WO 2005/022120 A2 | 3/2005 |
| WO | WO 2005/079202 A2 | 9/2005 |
| WO | WO 2005/086982 A2 | 9/2005 |
| WO | WO 2005/110624 A2 | 11/2005 |
| WO | WO 2006/069458 A1 | 7/2006 |
| WO | WO 2006/073420 A2 | 7/2006 |
| WO | WO 2006/078286 A2 | 7/2006 |
| WO | WO 2006/102064 A2 | 9/2006 |
| WO | WO 2007/024697 A2 | 3/2007 |
| WO | WO 2007/067922 A2 | 6/2007 |
| WO | WO 2007/106836 A2 | 9/2007 |
| WO | WO 2007/124612 A2 | 11/2007 |
| WO | WO 2008/051205 A2 | 5/2008 |
| WO | WO 2008/057615 A2 | 5/2008 |
| WO | WO 2008/060455 A3 | 5/2008 |
| WO | WO 2008/076473 A2 | 6/2008 |
| WO | WO 2008/091402 A2 | 7/2008 |
| WO | WO 2008/143714 A2 | 11/2008 |
| WO | WO 2008/150336 A2 | 12/2008 |
| WO | WO 2009/011450 A1 | 1/2009 |
| WO | WO 2009/023061 A2 | 2/2009 |
| WO | WO 2009/042079 A2 | 4/2009 |
| WO | WO 2008/106426 A9 | 10/2009 |
| WO | WO 2010/003212 A1 | 1/2010 |
| WO | WO 2010/048405 A1 | 4/2010 |
| WO | WO 2010/048407 A1 | 4/2010 |
| WO | WO 2010/056826 A1 | 5/2010 |
| WO | WO 2010/077226 A1 | 7/2010 |
| WO | WO 2010/093703 A1 | 8/2010 |
| WO | WO 2010/096035 A1 | 8/2010 |
| WO | WO 2012/069993 A2 | 5/2012 |
| WO | WO 2012/069992 A2 | 9/2012 |

OTHER PUBLICATIONS

International Search Report and Written Opinion dated Aug. 30, 2012, in Application No. PCT/IB2011/055240.
U.S. Appl. No. 09/213,781, filed Dec. 17, 1998, now U.S. Patent No. 6,332,110.
U.S. Appl. No. 10/055,225, filed Oct. 26, 2001, now U.S. Patent No. 6,560,543.
U.S. Appl. No. 10/392,112, filed Mar. 19, 2003, now U.S. Patent No. 7,454,295.
U.S. Appl. No. 10/695,627, filed Oct. 27, 2003, now U.S. Patent No. 6,954,701.
U.S. Appl. No. 11/331,721, filed Jan. 13, 2006.
U.S. Appl. No. 12/272,018, filed Nov. 17, 2008, now U.S. Patent No. 7,698,073.
U.S. Appl. No. 12/565,091, filed Sep. 23, 2009.
U.S. Appl. No. 12/710,451, filed Feb. 23, 2010.
U.S. Appl. No. 12/874,293, filed Sep. 2, 2010.
U.S. Appl. No. 12/952,566, filed Nov. 23, 2010.
U.S. Appl. No. 12/952,392, filed Nov. 23, 2010.
U.S. Appl. No. 13/620,000, filed Sep. 14, 2012.
U.S. Appl. No. 13/619,880, filed Sep. 14, 2012.
Cycliax, Ingo, "Remote Internet Data Logging and Sensing", Circuit Cellar Magazine, Embedded PC, PC/104 Quarter104, (Nov. 1997), pp. 53-59.
McKinnon, et al., "Automating Communications with and Developing User Interfaces for Remote data Acquisition and Analysis Systems", IEEE Transactions on Nuclear Science, vol. 44, No. 3, (Jun. 1997), pp. 1062-1064.
Franklin, et al., "Data in Your Face": Push Technology in Perspective, S., SIGMOD Record, vol. 27, Issue 2, (Jun. 1998), pp. 516-519.
Soreide, et al., "Mosaic Access to Realtime Data from the TOGA-TAO array of moored buoys", accessed from web site Equatorial Pacific, Oct. 16, 2002, pp. 1-8.
Northwest Fisheries Science Center, National Marine Fisheries Service (NOAA), "Water Recirculation Project", accessed from web site NWFSC:Aquaculture-Water Recirculation Project, Oct. 16, 2002, pp. 1-3.
Northwest Fisheries Science Center, "NWFSC Water Recirculation Project: Data Acquisition and Web Display", accessed from web site NWFSC Web Template, Oct. 16, 2002, pp. 1-3.
Scott, et al., "A Computer Automated Cold Water Recirculating System for Aquaculture Research", accessed from web U.S. Dept. Commerce/NOAA/NMFS/NWFSC, Oct. 16, 2002, pp. 1-9.
Remote Measurement Systems, "Case Studies", accessed from web site Remote Measurement Systems—Case Studies: Fisheries, Oct. 16, 2002, pp. 1-4.
Remote Measurement Systems, "Posting Real-Time Measurement to the Web", Home Energy, accessed from web site Posting Real-Time Measurements to Web Pages, Oct. 16, 2002, pp. 1-5.
Liu et al., Carbon Nanotube in Biology and Medicine: in vitro and in vivo Detection, Imaging and Drug Delivery; Nano Res., Vole 2, pp. 85-120 (2009).
Tzeng et al., "Hydration Properties of Carbon Nanotubes and Their Effects on Electrical and Biosensor Applications", New Diamond and Frontier Carbon Technology, vol. 14, No. 3, pp. 193-201, (2004).
Ardakan, Mohammad Mazloum et al.; "Novel Coated-Wire Membrane Sensor Based on Bis(Acetylacetonato) Cadmium(II) for the Determination of Chromate Ions"; Department of Chemistry, Faculty of Science, Kashan University, Kashan, Iran; received Jul. 24, 2004; accepted Nov. 16, 2004; published online Mar. 21, 2005 © Springer-Verlag 2005.
Schuler, R. et al., Modified gas-permeable silicone rubber membranes for covalent immobilization of enzymes and their use in biosensor development ICB, Institut fur Chemo- und Biosensorik, eV, Mendelstrasse 7, D-48149 Munster, Germany, received 13$^{th}$ Apr. 1999, accepted 18$^{th}$ Jun. 1999.
Faridbod, Farmoush et al.; "The fabrication of potentiometric membrane sensors and their applications"; Tehran, P.O. Box 14155-6451, Iran, accepted Nov. 12, 2007; African Journal of Biotechnology vol. 6 (25), pp. 2960-2987, Dec. 28, 2007. Available online at http://www.academicjournals.org/AJ; ISSN 1684-5315 © 2007 Academic Journals.
Zbignlew, Moron, "Considerations on the Accuracy of Measurements of Electrical Conductivity of Liquids" Department of Biomedical Engineering and Instrumentation, Wroclaw University of Technology, Wroclase, Poland, XVIII Imeko World Congress Metrology for a Sustainable Development, Sep. 17-22, 2006, Rio de Janeiro, Brazil.
Heng, Lee Yook et al., "Producing "Self-Plasticizing" Ion-Selective Membranes", Institute of Biotechnology, University of Cambridge, Tennis Court Road, Cambridge CB2 1QT, U.K. Anal. Chem. 2000, 72, 42-51.
Pretsch, Emo et al., "Design features of ionophores for ion selective electrodes", Department of Organic Chemistry, Swiss Federal Insti-

(56) References Cited

OTHER PUBLICATIONS tute of Technology (ETH), Universitatstrasse 16, CH-8092 Zurich, Switzerland, Pure & Appl. Chem., vol. 60, No. 4, pp. 567-574, 1988, printed in Great Britain © 1998 IUPAC.
Buhrer, Thomas, "Neutral-Carrier-Based Ion-Selective Microelectrodes Design and Application, A Review", Department of Organic Chemistry, Swiss Federal Institute of Technology, Zurich, Switzerland, Analytical Sciences, Dec. 1988, vol. 4, pp. 547-557.
French Search Report dated May 29, 2013, in French Patent Application No. 11 6066.
Nonfinal Office Action dated Jan. 31, 2013, in U.S. Appl. No. 13/619,880.
Nonfinal Office Action dated Mar. 5, 2013, in U.S. Appl. No. 13/620,000.
International Preliminary Report on Patentability dated Jun. 6, 2013, in PCT/IB2011/055240.
International Preliminary Report on Patentability dated Jun. 6, 2013, in PCT/IB2011/055238.
Final Rejection dated Jul. 19, 2013, in U.S. Appl. No. 13/619,880.
Lumb Alan M. et al., "Users Manual for an Expert System (HSPEXP) for Calibration of the Hydrological Simulation Program—Fortran", U.S. Geological Survey, Water-Resources Investigations Report 944168, 1994, 106 pages.
Johnston et al., "Management, Operation and Maintenance of Irrigation and Drainage Systems", Second Edition, ASCE Manuals and Reports on Engineering Practice No. 57, American Society of Civil Engineers, 1991, 13 pages.

\* cited by examiner

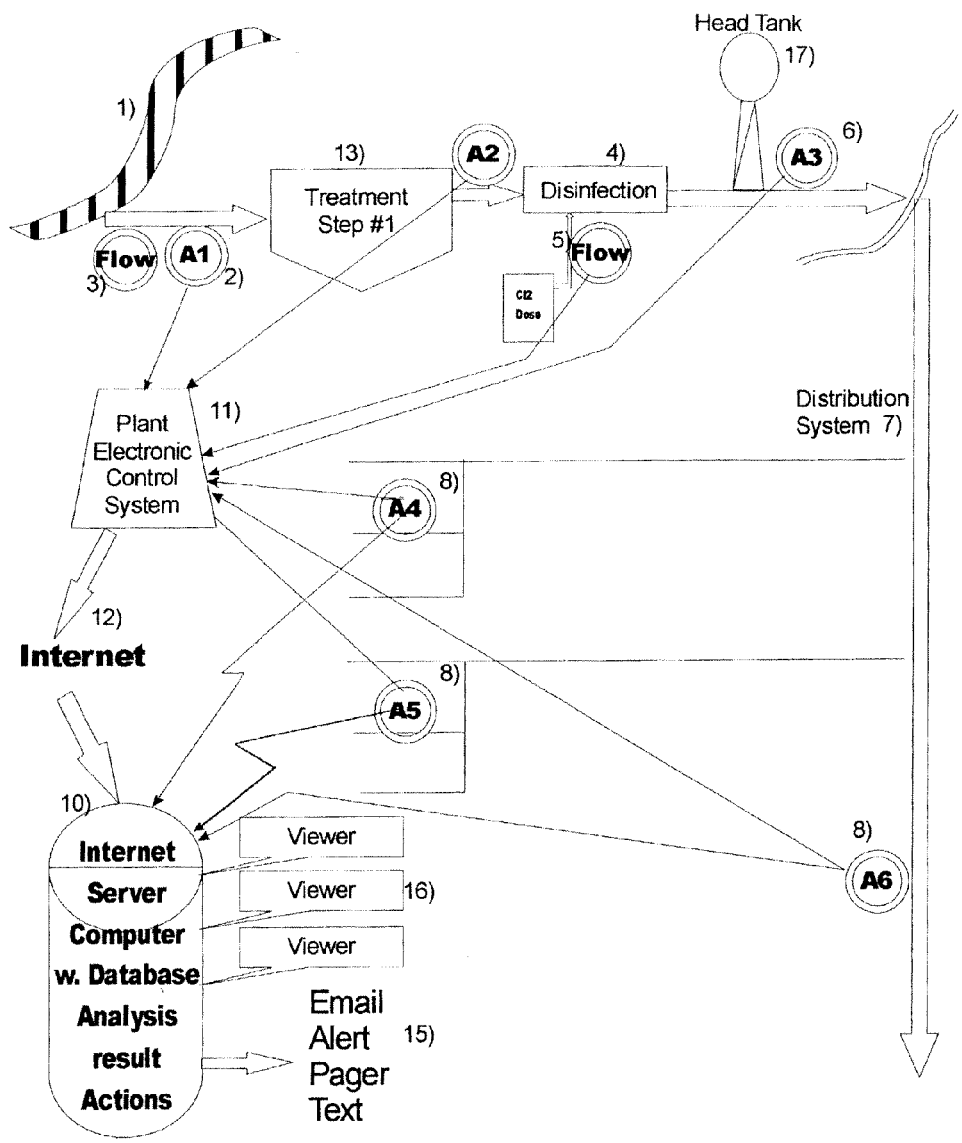

ANTI-TERRORISM WATER QUALITY MONITORING SYSTEM

CROSS-REFERENCE TO RELATED APPLICATIONS

This application is a continuation of application Ser. No. 12/710,451 filed Feb. 23, 2010, which is a divisional of application Ser. No. 12/272,018 filed Nov. 17, 2008 (now U.S. Pat. No. 7,698,073 issued Apr. 13, 2010), which is a continuation of application Ser. No. 10/392,112 filed Mar. 19, 2003 (now U.S. Pat. No. 7,454,295 issued Nov. 18, 2008), which is a continuation-in-part of application Ser. No. 10/055,225 filed Oct. 26, 2001 (now U.S. Pat. No. 6,560,543 issued May 6, 2003), which is a continuation-in-part of application Ser. No. 09/213,781 filed Dec. 17, 1998 (now U.S. Pat. No. 6,332,110 issued Dec. 18, 2001) the contents of all of which are incorporated herein by reference in their entireties.

FIELD OF THE INVENTION

This invention is related to the field of water treatment, and in particular, to a method of monitoring advanced separation and/or ion exchange processes by use of the world wide web allowing review of data collected and compiled asynchronously from a web server.

BACKGROUND OF THE INVENTION

Protection of water supplies from either inadvertent or deliberate contamination is an increasingly important concern. While there exist many different devices and methods to analyze water for contaminants, widespread deployment of such devices is expensive and difficult.

Most water treatment and distribution systems rely on the introduction and maintenance of a disinfectant into the water system to protect against biological and to a big extent chemical contamination. Chlorine, in the form of gas or hypochlorite, is by far the most common material used for this purpose. However, substitutes such as chloramines, ozone, hydrogen peroxide, peracetic acid, chlorine dioxide, and various mixed oxides also find service in this application. All of these materials have a more or less common mode of action. They rely on some sort of oxidation to effect the deactivation of biological organisms and the destruction of other organic compounds present in the water to be treated. The reaction rates of the various disinfection compounds are reasonably well known and well characterized.

Additionally, the presence or absence of turbidity in the water supply can greatly affect the amount of disinfectant required to achieve inactivation of biological organisms. The suspended particles producing turbidity are usually removed in the water treatment process before disinfection agents are applied. However, turbidity breakthroughs do occur and failure to quickly raise the disinfection dose level can lead to insufficient disinfection residuals reaching the distribution system. This can present a threat to public health, particularly if the drinking water supply is contaminated either deliberately or inadvertently.

To respond to the threats of terrorism in drinking water supplies, sensors have been and are being introduced into the distribution system to continuously monitor selected contaminants in the drinking water supply. For example a system may monitor free chlorine residual at a location in the distribution system downstream of the main treatment plant. However, the concentration of free chlorine present at this point in the distribution system may lag the free chlorine analyzed at the exit of the water treatment plant by hours or even days in some cases. The lag will also vary by time of day, since water demand follows well known 24 hour cyclical periods.

Applicant's invention registered as U.S. Pat. No. 6,332,110 teaches the use of a remote monitoring system to monitor the performance of an advanced separation process, particularly as related to water treatment. Many of the analytical devices used to continuously monitor water treatment operations are based on advanced separation processes employing selective ion membranes which concentrate the analyte for the detector apparatus. For example, detection of chlorine may be mediated via a membrane which readily and specifically passes free chlorine or hypochlorous acid (HOCl), thus separating the analyte from the bulk solution and concentrating it. The detector apparatus may incorporate multiple sensors and analyzers on a single unit. The multiple units are usually electronically controlled. The control system usually features output methods allowing the display and storage of collected data.

Deploying a range of sensor systems in the field provides a means to analyze for contaminants but does not provide for reporting and subsequent analysis of the data. Rapid reporting of the data to a facility readily accessible by the management or operators of the utility or distribution system and subsequent analysis of the data is very important to providing quick response in the event of a system contamination, either deliberate or otherwise.

The instant invention provides a means of rapidly aggregating the information at a central location in a form readily accessible to authorized users such as Homeland Security. It further provides a means to employ sophisticated statistical and data analysis techniques to the collected data. Since the central data collection server is connected to the internet, dispersion of alarms and alerts is greatly facilitated.

This invention consists of a method for collecting analytical data from the electronic control system of a single analyzer unit or multiple analyte units, storing the raw data locally for a short period of time, and subsequently using any of a variety of transmission means to send this data to a remote internet server computer. At the remote internet server computer, the data is stored in a database and may also be displayed via a web server. Upon arrival, or upon scheduled intervals, or upon a user request, the data is analyzed, compared to historical records, and a performance analysis result is made. Based upon the raw data or upon the analysis result, reports can be issued to appropriate regulatory agencies, alerts or alarms can be raised, and notifications issued via email, pager, voice or text messaging, or other messaging medium which can be mediated by a computer program connected to a phone line or the internet.

The methods used for data analysis can be readily varied or modified by someone skilled in the art of computer programming since the raw data is easily available from the database for manipulation. For example, the analytical data, when combined with known system constants such as flow rates, residence times, and so on, can be used to continuously generate a calculated product of disinfectant concentration times contact time C*T. This simple factor alone is quite useful in predicting the amount of biological organism deactivation. More sophisticated analyses can also be utilized. The results can be conveniently stored in the database and displayed as virtual sensors.

This invention is particularly useful when the same remote server computer has access to data from both the treatment facility and to analytical data from within the distribution system. In this case, historical information can be used to predict the expected conditions within the distribution system based on the effluent conditions from the treatment plant. The expected conditions can then be compared to the actual conditions in the distribution system. For example, in the instant invention, assume that data is being collected at the water treatment plant from the electronic control system about water flow rates, chemical dosing rates, filtered water turbidity, and chlorine residual. Also assume that data is also being collected from sensors in the distribution system reporting chlorine residual among other data. With current data and with historical data as a reference point, one can calculate a chlorine demand from the chemical dose rates, flows, and residual. Chlorine Demand is the actual amount of chlorine which is reacting, typically calculated as free chlorine dosed less the residual. Chlorine demand can be correlated with temperature, season, and filtered water turbidity. Additionally residual chlorine leaving the plant can be correlated with residual chlorine within the distribution system. If the actual chlorine residual measured at the distribution system point of measurement varies from the historical values expected from the chlorine residual leaving the treatment facility by more than a set percentage or more than a set number of standard deviations, then an alarm or alert may be issued by the monitoring system of the instant invention.

As a further example, consider the potential deliberate injection of chemically or biologically active agents into the distribution system at a point downstream of the treatment facility. A sophisticated terrorist may first inject a chlorine scavenger such as sodium metabisulfite into the distribution system to eliminate the chlorine residual normally present. At some point downstream of the metabisulfite injection point, the chemical or biological agent can be injected into the water without destruction by any residual disinfectant. Without an analytical station and monitoring system in place within the distribution system this approach could go undetected for quite some time, allowing a thorough infiltration of a biological or chemical agent throughout the distribution system. Assuming such an attack, the chlorine residual at the monitoring station would very quickly diminish to zero. A monitoring system with an active system in place to analyze the incoming data would quickly detect such an attack and sound the alarm. With historical data to compare to, the incidence of false terrorist attack alarms could be greatly diminished. For example a chlorine dosing equipment failure would be noticed at the water treatment plant providing information that a subsequent fall of chlorine concentration in the distribution system was not a terrorist attack, but an equipment failure.

In the same example of a hypothetical terrorist attack, the terrorist might try to simply overwhelm the residual chlorine in the distribution system by injecting, for example, an amount of biological or chemical agent dispersed as a fine powder in water. In this case, chlorine would fall as well but depending on the location of the sensors in relation to the injection point, the concentration might not fall to zero. However, the turbidity might well be affected. Thus a turbidity sensor in the distribution system would be an advantage in assessing a potential threat. In all cases, the need to quickly transmit raw data from both the distribution system and treatment plant to a computer system where it can be manipulated and analyzed is very important for prompt action to occur in response Co any threat Co the water system.

SUMMARY OF THE INVENTION

The instant invention is a method for continuously monitoring a water treatment system and related distribution network providing potable water to a municipality, city, housing development or other potable water consumer. The method includes the collection of data from the distribution system and in the preferred embodiment from the water treatment facility as well. The method also includes the collection of data from advanced separation processes which are integrated into analytical instruments. The data collected are stored in a remote database on a remote server computer or bank of computers.

The data are manipulated to generate preconfigured performance, maintenance, quality assurance, quality control, regulatory, performance graphing, historical trends, and regulatory reports. The data is collected from sensors located at an equipment site and transferred to a remotely located computer using transmission means by use of the Internet where all data received can be used for the generation of reports which are accessible by Internet connection. The reports, graphs and information can be viewed online or downloaded by use of a web browser. Regulatory reports can be forwarded automatically to the regulatory agency via electronic transmission means with the added benefit of receiving reports generated directly from the sensor input thereby eliminated the possibility of human error or tampering. The method allows a single location to monitor countless customers with each customer capable of reviewing information relevant to their equipment. All information is kept confidential by use of appropriate account names, protocols and passwords.

Thus, an objective of the invention of utmost importance for security concerns is to use the data manipulation steps to continuously compare the current water treatment facility data with current data obtained from the distribution system to each other and to historical records of performance already stored in the database. As will be readily appreciated by those skilled in the art of data analysis, this can provide a powerful indicator of either normal response in the distribution system or out of bounds conditions that may require immediate notification of responsible parties preferably by direct contact with Homeland Security.

Another objective of the invention is to provide a means for analytical devices using advanced separation processes such as ion selective membranes or electrodialysis membranes to rapidly and securely transmit their data to a remote database server computer for data manipulation and display on the World Wide Web.

Another objective of the invention is to provide a facile means to evaluate the conditions in the water treatment distribution systems as to health and safety concerns and allow this information to be shared by responsible parties via the World Wide Web.

Yet another feature and objective of the invention is to provide a means of remote monitoring advanced separation processes, water, and wastewater treatment plants in a manner that prevents any possible hacker attack to the electronic control system of the plant or process being monitored. The use of a remote database and web server allows viewers near real time access to plant performance but only allows access to web pages, not the control system. In more conventional remote monitoring applications, users or viewers need to actually connect with the computer or electronic control system which is actually controlling the plant. Thus, compromised passwords could result in an unauthorized user seizing control of the control system. In the instant invention, the control system need not be configured for remote access at all. In the instant invention, a compromised password will merely allow a remote user to see data from the process but not control any part of process, nor actually make any connection to the electronic control system of the facility, or computer attached to the electronic control system.

BRIEF DESCRIPTION OF THE DRAWING

FIG. 1 is a flow diagram of a conventional water treatment facility and distribution system with the interfaced anti-terrorism quality monitoring system of the instant invention.

DETAILED DESCRIPTION OF THE PREFERRED EMBODIMENT

Referring to FIG. 1, which shows a typical water treatment facility and distribution system, water from the supply (1) is pumped to the treatment plant. Analyzer A1 (2) and flow meter (3) collect data on the raw water supply. Analyzer A1, analyzing for turbidity, temperature, and possibly TOC (Total Organic Carbon) are not strictly necessary but if present provide better predictive reliability.

Treatment step (13) typically consists of settling and filtration to remove suspend matter. Analyzer A2 (14) monitors the efficiency of the treatment step. Disinfection step (4) allows chlorine dosed from the chlorine dosing station (5) to contact the water for a period of time, variable depending on temperature and organic matter loading in the supply water. Analyzer A3 (6) verifies that the disinfection step is working by measuring chlorine residual before entering the distribution system (7).

Analyzers A4, A5, and A6 (8) analyze for chlorine residual in the distribution system. Multifunction analyzers, the so called ab on a chip could also be used in the distribution system to analyze for constituents in addition to chlorine.

Data from the water treatment system is typically collected by a SCADA or other electronic control system (11) allowing local operators to operate and control the plant. Analyzers in the distribution system can be fitted to either send data to the treatment plant SCADA system or to the remote Database and Web Servers (10) of the instant invention. Data sending can be via transmission methods to the internet then subsequently via the Internet to said remote database and web servers.

At the said remote database and web servers, the data is manipulated, reported, and displayed for various authorized viewers and users (16). If the data manipulation indicates that alarms or alerts are warranted, the software in the database can send the appropriate notices (15). As can be readily appreciated there are many different permutations and combinations of the above system which will be obvious to someone skilled in the art of water treatment and in the art of remote monitoring. No matter the permutations, key features of the instant invention remain the same. For example, the distribution system may incorporate various additional pumping stations or head tanks (17). Similarly, the transmission methods used by the instruments and analyzers in the water, treatment system and in the water distribution system used to send data to either the remote database and web servers or to the SCADA system at the treatment facility can vary. For example, cellular phones can be used to dial either local or central Internet services providers. Radios, or so called remote terminal units (RTU) coupled to radio frequency transmitters, can also be used to send transfer the collected data to SCADA system or can send it directly to the said remote database.

I claim:

1. A system for real-time web-based monitoring of water utilities, the system comprising:
   at least one data detection device configured to:
      continuously scan sensor data input and send the inputted sensor data to a data management device;
      receive sensor and operational data relevant to monitoring the water in a water utility system;
      manipulate the received sensor and operational data; and
      store the manipulated data; and
   a data management device configured to:
      receive the manipulated data sent from the data detection device;
      evaluate the received data by continuously comparing the received sensor data with set alarm points;
      manipulate the evaluated data into an analysis result;
      display the analysis result and historical data in a color-coded graphical user interface, indicating normal system operation warning status, and alarm conditions;
      the analysis result being continuously updated based on the incoming data and displayed in a graphical or tabular format such that an individual having been authorized to access the analysis result can assess a current state of the system performance based on the display; and
      determine that an individual is authorized to receive the analysis result.

2. The system of claim 1, wherein the data detection device is configured to send the stored data via an ftp protocol.

3. The system of claim 1, wherein the customized report includes a work order with predefined inspection checklist.

4. The system of claim 1, wherein the customized report includes a summary of work order and maintenance schedule.

5. The system of claim 1, wherein the customized report includes a regulatory compliance report.

6. The system of claim 1, wherein the customized report includes a trend modeling report when conditions appear likely to exceed normal alarm conditions.

7. The system of claim 1, wherein the customized report includes a financial oversight report.

8. The system of claim 1, wherein the customized report includes an exception report indicating instances where conditions were close to triggering an alarm.

9. The system of claim 1, wherein the data management device is further configured to display the historical data in a geographical form.

10. A system for real-time web-based monitoring of water utilities, the system comprising:
    at least one data detection device configured to:
       receive sensor and operational data relevant to monitoring the water in a water utility system; and
    a data management device separate from the data detection device and configured to:
       receive the data from the data detection device;
       evaluate the received data;
       manipulate the evaluated data into an analysis result;
       display the analysis result in a user interface; and
       automatically send information relating to the analysis result to authorized individuals;
       wherein the data detection device is configured to continuously scan sensor data input and send the inputted sensor data to the data management device, and
       the data management device is configured to continuously compare the received sensor data with set alarm points and update the display based on newly received sensor data from the detection device.

11. The system of claim 10, wherein the data management device is further configured to display data in a geographical form.

12. The system of claim 10, wherein the sending of the information includes automatically sending the information to the authorized individuals using multimedia messaging including e-mail, pager, or facsimile.

13. The system of claim 10, wherein the data management device is further configured to display the analysis result graphically in a multi-color tabular format indicating normal system operation, warning status, and alarm condition.

14. The system of claim 10, wherein the data management device is further configured to display historical data concerning the water management system.

15. The system of claim 10, wherein the data management device is further configured to display historical data in a geographical form.

16. A system for real-time web-based monitoring of water utilities, the system comprising:
a web-based data management device configured to:
obtain periodically from one or more remote sources data based on water quality sensor readings;
compile the data into a database;
update the compiled data based on new data from the one or more remote sources;
analyze the compiled data to determine whether a predetermined alarm condition exists and whether the alarm condition satisfies a predefined requirement;
format the analyzed data into a color coded graphical display indicating normal system operation, warning status, and alarm conditions, such that an individual having been authorized to access the web-based management device can assess a current state of the system performance based on the display;
generate a customized report based on the analyzed data;
send the customized report to pre-selected recipients if the alarm condition satisfies the predefined requirement;
display the analysis result in a user interface;
continuously update the analysis result based on the updated compiled data; and
send information relating to the analysis result to authorized individuals.

17. The system of claim 16, wherein the customized report includes a regulatory compliance report.

18. The system of claim 16, wherein the customized report includes an exception report indicating instances where conditions were close to triggering an alarm.

19. The system of claim 16, wherein the information consists of an alarm signal.

* * * * *